US008734393B2

(12) United States Patent
Cleathero

(10) Patent No.: US 8,734,393 B2
(45) Date of Patent: May 27, 2014

(54) AUTOINJECTOR

(75) Inventor: Ian Cleathero, Melton Mowbray (GB)

(73) Assignee: The Medical House Limited (GB)

( * ) Notice: Subject to any disclaimer, the term of this patent is extended or adjusted under 35 U.S.C. 154(b) by 81 days.

(21) Appl. No.: 13/265,801

(22) PCT Filed: Apr. 15, 2010

(86) PCT No.: PCT/GB2010/050619
§ 371 (c)(1),
(2), (4) Date: Feb. 10, 2012

(87) PCT Pub. No.: WO2010/122323
PCT Pub. Date: Oct. 28, 2010

(65) Prior Publication Data
US 2012/0136303 A1    May 31, 2012

(30) Foreign Application Priority Data
Apr. 23, 2009  (GB) .................................. 0906973.3

(51) Int. Cl.
*A61M 37/00*    (2006.01)
*A61M 5/20*    (2006.01)

(52) U.S. Cl.
USPC ........... 604/131; 604/135; 604/136; 604/143; 604/144; 604/156

(58) Field of Classification Search
USPC .......... 604/134–136, 140, 143, 144, 157, 220
See application file for complete search history.

(56) References Cited

U.S. PATENT DOCUMENTS

| 60,917 A | 1/1867 | Brown |
|---|---|---|
| 3,702,608 A | 11/1972 | Tibbs |

(Continued)

FOREIGN PATENT DOCUMENTS

| DE | 102004060146 | 8/2005 |
|---|---|---|
| EP | 0453212 | 10/1991 |

(Continued)

OTHER PUBLICATIONS

"relaxed." Merriam-Webster Dictionary, found on-line at http://www.merriam-webster.com/dictionary/relaxed, 6 pages.

(Continued)

*Primary Examiner* — Jason Flick
*Assistant Examiner* — Leah Stohr
(74) *Attorney, Agent, or Firm* — Sheridan Ross P.C.

(57) ABSTRACT

An injection device comprising an outer housing adapted to receive a syringe for holding a volume of a medicament, said syringe comprising a barrel, a needle at one end of the barrel, and a plunger, axially moveable within the barrel, the needle and barrel being such that at least part of the needle is axially moveable in and out of said outer housing but is biased to be normally wholly inside said housing. The injection device further comprises an inner housing intermediate the outer housing and at least part of the barrel and/or plunger, an energy source in communication with the inner housing, and blocking means capable of preventing said inner housing moving axially under the influence of said energy source. The device is moveable between two positions, namely a first position in which the inner housing is prevented from moving axially forward by engagement with said blocking means; and a second position in which the inner housing is disengaged from said blocking means and is capable of acting on the syringe under the influence of said energy source to move said at least part of the needle out of said outer housing. The device is moveable from said first position to said second position by movement of said outer housing relative to said inner housing and actuation of a trigger.

21 Claims, 3 Drawing Sheets

(56) References Cited

U.S. PATENT DOCUMENTS

| | | | |
|---|---|---|---|
| 3,756,242 A | 9/1973 | Coss | |
| 3,797,489 A | 3/1974 | Sarnoff | |
| 3,811,442 A | 5/1974 | Maroth | |
| 4,617,016 A | 10/1986 | Blomberg | |
| 4,913,699 A | 4/1990 | Parsons | |
| 4,923,447 A | 5/1990 | Morgan | |
| 4,958,622 A | 9/1990 | Selenke | |
| 4,976,724 A | 12/1990 | Nieto et al. | |
| 5,000,744 A | 3/1991 | Hoffman et al. | |
| 5,024,656 A | 6/1991 | Gasaway et al. | |
| 5,042,977 A | 8/1991 | Bechtold et al. | |
| 5,078,698 A | 1/1992 | Stiehl et al. | |
| 5,167,632 A | 12/1992 | Eid et al. | |
| 5,211,625 A | 5/1993 | Sakurai et al. | |
| 5,300,030 A | 4/1994 | Crossman et al. | |
| 5,320,609 A | 6/1994 | Haber et al. | |
| 5,478,316 A | 12/1995 | Bitdinger et al. | |
| 5,568,261 A | 10/1996 | Wakai et al. | |
| 5,599,309 A | 2/1997 | Marshall et al. | |
| 5,634,906 A | 6/1997 | Haber et al. | |
| 5,658,261 A | 8/1997 | Neer et al. | |
| 5,681,291 A | 10/1997 | Galli | |
| 5,779,675 A | 7/1998 | Reilly et al. | |
| 5,779,677 A | 7/1998 | Frezza | |
| 6,203,530 B1 | 3/2001 | Stewart, Sr. | |
| 6,210,369 B1 | 4/2001 | Wilmot et al. | |
| 6,264,629 B1 | 7/2001 | Landau | |
| 6,270,479 B1 | 8/2001 | Bergens et al. | |
| 6,280,421 B1 | 8/2001 | Kirchhofer et al. | |
| 6,544,234 B1 | 4/2003 | Gabriel | |
| 6,605,072 B2 | 8/2003 | Struys et al. | |
| 6,607,510 B2 | 8/2003 | Landau | |
| 6,620,137 B2 | 9/2003 | Kirchhofer et al. | |
| 6,632,198 B2 | 10/2003 | Caizza | |
| 6,656,163 B1 | 12/2003 | Marshall et al. | |
| 6,689,093 B2 | 2/2004 | Landau | |
| 6,752,781 B2 | 6/2004 | Landau et al. | |
| 6,981,499 B2 | 1/2006 | Anderson et al. | |
| 7,118,552 B2 | 10/2006 | Shaw et al. | |
| 7,156,823 B2 | 1/2007 | Landau et al. | |
| 7,635,356 B2 | 12/2009 | Stamp | |
| 7,645,265 B2 | 1/2010 | Stamp | |
| 7,976,499 B2 | 7/2011 | Grunhut et al. | |
| 8,187,226 B2 | 5/2012 | Stamp et al. | |
| 8,308,697 B2 | 11/2012 | Stamp et al. | |
| 2001/0005781 A1 | 6/2001 | Bergens et al. | |
| 2003/0105430 A1 | 6/2003 | Lavi et al. | |
| 2003/0236502 A1 | 12/2003 | De la Serna et al. | |
| 2004/0039336 A1* | 2/2004 | Amark et al. | 604/136 |
| 2005/0027255 A1 | 2/2005 | Lavi et al. | |
| 2005/0165349 A1 | 7/2005 | Stamp | |
| 2006/0100589 A1 | 5/2006 | Lin | |
| 2006/0270984 A1 | 11/2006 | Hommann | |
| 2007/0017533 A1 | 1/2007 | Wyrick | |
| 2007/0173770 A1 | 7/2007 | Stamp | |
| 2007/0265568 A1 | 11/2007 | Tsals et al. | |
| 2008/0195056 A1* | 8/2008 | Bishop et al. | 604/218 |
| 2009/0012471 A1 | 1/2009 | Harrison | |
| 2010/0069846 A1 | 3/2010 | Stamp | |
| 2010/0152655 A1 | 6/2010 | Stamp | |
| 2011/0282278 A1 | 11/2011 | Stamp et al. | |
| 2011/0306938 A1 | 12/2011 | Cleathero | |
| 2012/0130342 A1 | 5/2012 | Cleathero | |

FOREIGN PATENT DOCUMENTS

| | | |
|---|---|---|
| EP | 0518416 | 12/1992 |
| EP | 0740942 | 11/1996 |
| EP | 0864335 | 9/1998 |
| EP | 1323447 | 7/2003 |
| EP | 1323477 | 7/2003 |
| EP | 2080532 | 7/2009 |
| FR | 2899482 | 10/2007 |
| GB | 886444 | 1/1962 |
| GB | 2388033 | 11/2003 |
| GB | 2396298 | 6/2004 |
| GB | 2397767 | 8/2004 |
| GB | 2410188 | 7/2005 |
| GB | 2414398 | 11/2005 |
| GB | 2443606 | 5/2008 |
| WO | WO 94/21316 | 9/1994 |
| WO | WO 99/10030 | 3/1999 |
| WO | WO 99/22792 | 5/1999 |
| WO | WO 00/09186 | 2/2000 |
| WO | WO 01/93926 | 12/2001 |
| WO | WO 02/17996 | 3/2002 |
| WO | WO 02/47746 | 6/2002 |
| WO | WO 02/070051 | 9/2002 |
| WO | WO 03/097133 | 11/2003 |
| WO | WO 03/099358 | 12/2003 |
| WO | WO 2004/108194 | 12/2004 |
| WO | WO 2005/009515 | 2/2005 |
| WO | WO 2005/009520 | 2/2005 |
| WO | WO 2005/046765 | 5/2005 |
| WO | WO 2005/070481 | 8/2005 |
| WO | WO 2005/097252 | 10/2005 |
| WO | WO 2005/115507 | 12/2005 |
| WO | WO 2005/115512 | 12/2005 |
| WO | WO 2006/052737 | 5/2006 |
| WO | WO 2006/106291 | 10/2006 |
| WO | WO 2006/106295 | 10/2006 |
| WO | WO 2006/111862 | 10/2006 |
| WO | WO 2007/008257 | 1/2007 |
| WO | WO 2007/036676 | 4/2007 |
| WO | WO 2007/083115 | 7/2007 |
| WO | WO 2007/132353 | 11/2007 |
| WO | WO 2008/075033 | 6/2008 |
| WO | WO 2008/107670 | 9/2008 |
| WO | WO 2008/113864 | 9/2008 |
| WO | WO 2010/026414 | 3/2010 |

OTHER PUBLICATIONS

Authorized Officer Reinbold, International Preliminary Report on Patentability for International (PCT) Patent Application No. PCT/GB2005/000223, mailed Jan. 23, 2006, 6 pages.

Authorized Officer Reinbold, Written Opinion for International (PCT) Patent Application No. PCT/GB2005/000223, mailed Jun. 22, 2005, 7 pages.

UK Search Report for Application No. GB0602411.1, dated Apr. 7, 2006, 4 pages.

Corrected Search Report under Section 17 for Application No. GB0620163.6, dated Nov. 24, 2006, 1 page.

International Search Report for International (PCT) Patent Application No. PCT/GB2007/000141, mailed May 5, 2007, 2 pages.

Authorized Officer Bjorklund, Written Opinon for International (PCT) Patent Application No. PCT/GB2007/000141, mailed May 5, 2007, 7 pages.

Authorized Officer Mulhausen, International Preliminary Report on Patentability for International (PCT) Patent Application No. PCT/GB2007/000141, mailed Jul. 29, 2008, 8 pages.

Authorized Officer Reinbold, International Search Report issued by the European Patent Office on Mar. 19, 2008 for International Application No. PCT/GB2007/004870, 3 pages.

Authorized Officer Reinbold, Written Opinion issued by the European Patent Office on Mar. 19, 2008 for International Application No. PCT/GB2007/004870, 7 pages.

Authorized Officer Mulhausen, International Preliminary Report on Patentability issued on Jun. 24, 2009 for International Application No. PCT/GB2007/004870, 8 pages.

Authorized Officer Guidoin, International Search Report for International (PCT) Application No. PCT/GB2008/000741, mailed Dec. 23, 2008, 8 pages.

Authorized Officer Urack, Written Opinion for International (PCT) Patent Application No. PCT/GB2008/00741, mailed Dec. 23, 2008, 15 pages.

Authorized Officer Mulhausen, International Preliminary Report on Patentability for International (PCT) Application No. PCT/GB2008/000741, mailed Sep. 17, 2009, 13 pages.

(56) References Cited

OTHER PUBLICATIONS

UK Search Report for Application No. GB0804021.4, dated Jul. 1, 2008, 4 pages.
UK Search Report for Application No. GB0704351.6, dated Jun. 7, 2007, 4 pages.
Formalities Officer Sulis, Communication pursuant to Rule 114(2) EPC for European Patent Application No. 07704923.7, mailed Sep. 29, 2010, 9 pages.
Communication pursuant to Article 94(3) EPC for European Patent Application No. 07704923.7, dated Aug. 2, 2011, 7 pages.
Authorized Officer Bjorklund, International Search Report issued by the European Patent Office for International (PCT) Application No. PCT/GB2009/051716, mailed May 19, 2010, 5 pages.
Authorized Officer Mulhausen, International Preliminary Report on Patentability for International (PCT) Application No. PCT/GB2009/051716, issued Jun. 21, 2011, 9 pages.
Authorized Officer Reinbold, International Search Report for International Application No. PCT/GB2010/050161, dated May 17, 2010, 5 pages.
Authorized Officer Reinbold, Written Opinion for International Application No. PCT/GB2010/050161, issued Aug. 5, 2011, 5 pages.
Authorized Officer Mulhausen, International Preliminary Report on Patentability issued on Aug. 9, 2011 for International Application No. PCT/GB2010/050161, 6 pages.
Official Action for U.S. Appl. No. 10/767,859, mailed Feb. 24, 2006, 8 pages.
Official Action for U.S. Appl. No. 10/767,859, mailed Sep. 12, 2006, 10 pages.
Official Action for U.S. Appl. No. 10/767,859, mailed Jun. 5, 2007, 8 pages.
Official Action for U.S. Appl. No. 10/767,859, mailed Dec. 28, 2007, 8 pages.
Official Action for U.S. Appl. No. 10/767,860, mailed Mar. 14, 2006, 8 pages.
Official Action for U.S. Appl. No. 10/767,860, mailed Aug. 22, 2006, 8 pages.
Official Action for U.S. Appl. No. 10/767,860, mailed Dec. 15, 2006, 3 pages.
Official Action for U.S. Appl. No. 10/767,860, mailed Apr. 10, 2007, 7 pages.
Official Action for U.S. Appl. No. 10/767,860, mailed Sep. 24, 2007, 9 pages.
Official Action for U.S. Appl. No. 10/767,860, mailed Jan. 11, 2008, 8 pages.
Official Action for U.S. Appl. No. 10/767,860, mailed Jun. 12, 2008, 6 pages.
Advisiory Action for U.S. Appl. No. 10/767,860, mailed Sep. 5, 2008, 3 pages.
Offical Action for U.S. Appl. No. 10/767,860, mailed Dec. 2, 2008, 5 pages.
Interview Summary for U.S. Appl. No. 10/767,860, mailed Feb. 2, 2009, 4 pages.
Notice of Allowance for U.S. Appl. No. 10/767,860, mailed Aug. 27, 2009, 8 pages.
Restriction Requirement for U.S. Appl. No. 11/387,645, mailed May 28, 2009, 7 pages.
Official Action for U.S. Appl. No. 11/387,645, mailed May 25, 2010, 16 pages.
Official Action for U.S. Appl. No. 11/387,645, mailed Sep. 17, 2010, 29 pages.
Official Action for U.S. Appl. No. 11/387,645, mailed Feb. 11, 2011, 29 pages.
Official Action for U.S. Appl. No. 11/387,645, mailed Jul. 14, 2011, 19 pages.
Official Action for U.S. Appl. No. 11/387,645, mailed Dec. 21, 2011, 21 pages.
Official Action for U.S. Appl. No. 10/597,379, mailed Jul. 31, 2008, 12 pages.
Official Action for U.S. Appl. No. 10/597,379, mailed Feb. 23, 2009, 9 pages.
Notice of Allowance for U.S. Appl. No. 10/597,379, mailed Sep. 2, 2009, 11 pages.
Restriction Requirement for U.S. Appl. No. 12/623,960, mailed Jan. 5, 2012, 6 pages.
Official Action for U.S. Appl. No. 12/623,960, mailed Mar. 5, 2012, 11 pages.
Official Action for U.S. Appl. No. 12/161,776, mailed Oct. 6, 2010, 10 pages.
Official Action for U.S. Appl. No. 12/161,776, mailed May 11, 2011, 11 pages.
Official Action for U.S. Appl. No. 12/161,776, mailed Aug. 29, 2012, 8 pages.
Official Action for U.S. Appl. No. 12/530,107, mailed Apr. 14, 2011, 10 pages.
Official Action for U.S. Appl. No. 12/530,107, mailed Aug. 4, 2011, 9 pages.
Notice of Allowance for U.S. Appl. No. 12/530,107, mailed Jan. 25, 2012, 8 pages.
Official Action for U.S. Appl. No. 13/189,286, mailed Jan. 4, 2012, 9 pages.
Notice of Allowance for U.S. Appl. No. 13/189,286, mailed Jun. 22, 2012, 6 pages.
Search Report prepared by the United Kingdom Intellectual Property Office on Aug. 27, 2009, for Application No. GB0906973.3.
Official Action for U.S. Appl. No. 13/147,568 mailed Sep. 6, 2013, 10 pages.
Notice of Allowance for U.S. Appl. No. 12/161,776, mailed Jun. 7, 2013, 9 pages.
Official Action for U.S. Appl. No. 12/601,220 mailed Jun. 27, 2013, 12 pages.
Official Action for U.S. Appl. No. 11/387,645, mailed Nov. 12, 2013, 13 pages.
Notice of Allowance for U.S. Appl. No. 12/161,776, mailed Oct. 15, 2013, 10 pages.
Official Action for U.S. Appl. No. 13/147,568 mailed Oct. 23, 2013, 8 pages.

\* cited by examiner

AUTOINJECTOR

CROSS REFERENCE TO RELATED APPLICATIONS

This application is a national stage application under 35 U.S.C. 371 of PCT Application No. PCT/GB2010/050619 having an international filing date of 15 Apr. 2010, which designated the United States, which PCT application claimed the benefit of Great Britain Application No. 0906973.3 filed 23 Apr. 2009, the entire disclosure of each of which are hereby incorporated by reference.

This invention relates to injection devices and more specifically to autoinjector devices for the administration of liquid medication, for example, insulin or growth hormone.

BACKGROUND

Many types of autoinjector devices exist for providing an automatic means for delivering a dose of medicament. An example of a known autoinjector device is described in the applicant's granted European Patent EP-B-1715903 (The Medical House plc).

Many autoinjectors described in the prior art comprise an energy source such as a spring or compressed gas that is actuated by a user to drive the needle into the injection site and deliver a dose of medicament. For example, in EP-B-1715903, the delivery of medicament is actuated by sliding an outer housing relative to other components of the device towards the injection site. In other devices, a button is pressed to release stored energy and initiate delivery of the medicament.

In UK patent GB-B-2239180 (Glaxo Group Limited), a self-injecting device is described that has a trigger, a release mechanism and separate means, controlled by the release mechanism, to discharge medicament. The device has a body formed from two parts that are moveable with respect to one another. The discharge means are actuated by operation of the trigger and release mechanism, and movement of one part of the body relative to the other part.

The actuation means in prior art autoinjectors varies between devices and the choice of actuation means is usually based on technical considerations such as ease of operation. However, it is found that actuation means that are easy to operate are susceptible to accidental delivery of medicament which may be dangerous. To overcome this problem, some autoinjector devices incorporate safety catches or locks that prevent accidental actuation. In these devices, the safety catch must be disengaged before the device can be actuated using the usual actuation means. The disengaging of a safety catch or similar mechanism adds an extra step to the actuation process. The extra step may be complicated and unintuitive and may not allow for a sufficiently quick delivery of a dose of medicament in an emergency situation where the user may be panicked and/or suffering.

BRIEF SUMMARY OF THE DISCLOSURE

In accordance with the present invention there is provided an injection device comprising an outer housing adapted to receive:
a syringe for holding a volume of a medicament, said syringe comprising a barrel, a needle at one end of the barrel, and a plunger, axially moveable within the barrel, the needle and barrel being such that at least part of the needle is axially moveable in and out of said outer housing but is biased to be normally wholly inside said housing;
the injection device further comprising:
an inner housing intermediate the outer housing and at least part of the barrel and/or plunger;
an energy source in communication with the inner housing; and
blocking means capable of preventing said inner housing moving axially under the influence of said energy source;
the device being moveable between two positions, namely
a first position in which the inner housing is prevented from moving axially forward by engagement with said blocking means; and
a second position in which the inner housing is disengaged from said blocking means and is capable of acting on the syringe under the influence of said energy source to move said at least part of the needle out of said outer housing;
wherein said device is moveable from said first position to said second position by movement of said outer housing relative to said inner housing and actuation of a trigger.

The user must then perform two actions, namely move the outer housing relative to the inner housing and actuate the trigger to move the device from the first position to second position. A result of this is that the risk of accidental firing is reduced.

Preferably, the inner housing is biased axially forward by said energy source in said first position so that upon disengagement of the inner housing from the blocking means, the inner housing is immediately urged axially forward under the influence of the energy source. In one particularly preferable embodiment, the energy source is a spring. In an alternative preferable embodiment, the energy source is compressed gas.

The device preferably further comprises a spring housing intermediate said outer housing and said inner housing that may serve as a surface for the energy source to act against.

In one particularly preferable embodiment, the blocking means prevent said inner housing moving axially forward under the influence of said energy source by blocking the axial path of at least part of said inner housing. In this embodiment, the inner housing is prevented from forward axial movement by axially abutting the blocking means.

In an alternative preferable embodiment, the blocking means comprises a radially moveable component that can be radially urged against a surface of said inner housing so that friction prevents said inner housing moving axially forward under the influence of said energy source. In this alternative embodiment, the inner housing is axially restrained through friction and not axial abutment. In a further alternative embodiment, the inner housing may be axially restrained by a combination of friction and abutment. In any embodiment, the blocking means prevent the inner housing from moving axially forward under the influence of the energy source.

Preferably, the trigger comprises a disengagement element and, upon actuation of the trigger, said disengagement element is capable of disengaging said inner housing from said blocking means to allow said device to move into said second position. In the case where the inner housing is axially restrained through axial abutment with the blocking means, the disengagement element preferably comprises axially extending ribs. Preferably the ribs are axially moveable with respect to said inner housing and are adapted to disengage said inner housing from said blocking means upon axially moving relative to said inner housing.

Further preferably, the ribs disengage said inner housing from said blocking means upon axially moving relative to said inner housing by a disengagement distance; and in said first position, said ribs are axially moveable relative to said outer housing by a first distance and said outer housing is axially moveable relative to said inner housing by a second distance;

where said first distance plus said second distance is greater than or equal to said disengagement distance. In the first position, axial movement of said ribs is preferably limited relative to said outer housing to not exceed said first distance, and axial movement of said outer housing is preferably limited relative to said inner housing to not exceed said second distance. Preferably, the axial movement of said ribs is limited relative to said outer housing and axial movement of said outer housing is limited relative to said inner housing by at least one catch on said outer housing;

where each of said at least one catch has an axially extending portion that abuts said spring housing or a component fixed axially thereto to limit relative displacement between said outer housing and said inner housing, and a radially extending portion that is in axial alignment with at least a portion of said trigger to limit relative displacement between said ribs and said outer housing. In these preferable embodiments, the individual action of moving the outer housing relative to the inner housing or moving the ribs relative to the outer housing are insufficient to cause the ribs to disengage the inner housing from the blocking means. The user must therefore perform two distinctly different actions to deliver a dose of medicament.

In a particularly preferable embodiment, the trigger means comprises a button and said trigger means is actuated by depressing said button. In this embodiment, the exterior of the device will resemble some button-actuated prior art autoinjector devices whilst the inner mechanism may be distinctly different. Preferably, the button is connected to said ribs and depression of said button proportionally moves said ribs axially forward relative to said outer housing. In one embodiment, the user must depress the button by an amount equal to the first distance to move the ribs relative to the outer housing by the first distance. Further preferably the inner housing comprises a plurality of radially flexible tags, and said blocking means comprises apertures in said spring housing for receiving said flexible tags and preventing forward axial movement of said inner housing in said first position. The ribs are preferably adapted to contact said flexible tags and cause said tags to flex radially inwards, out of said apertures, to disengage said inner housing from said blocking means.

When the device is in the second position with the inner housing disengaged from the blocking means, the inner housing preferably acts on the barrel of said syringe to move said at least part of the needle out of said outer housing so that the needle may penetrate an injection site. From said second position, the device is preferably moveable into a third position in which the inner housing acts on the plunger but not the barrel such that, in use, said plunger is moveable axially into said barrel so as to expel medicament through the needle and a dose of medicament may be delivered to the injection site.

BRIEF DESCRIPTION OF THE DRAWINGS

Embodiments of the invention are further described hereinafter with reference to the accompanying drawings, in which.

DETAILED DESCRIPTION

Figure 1:
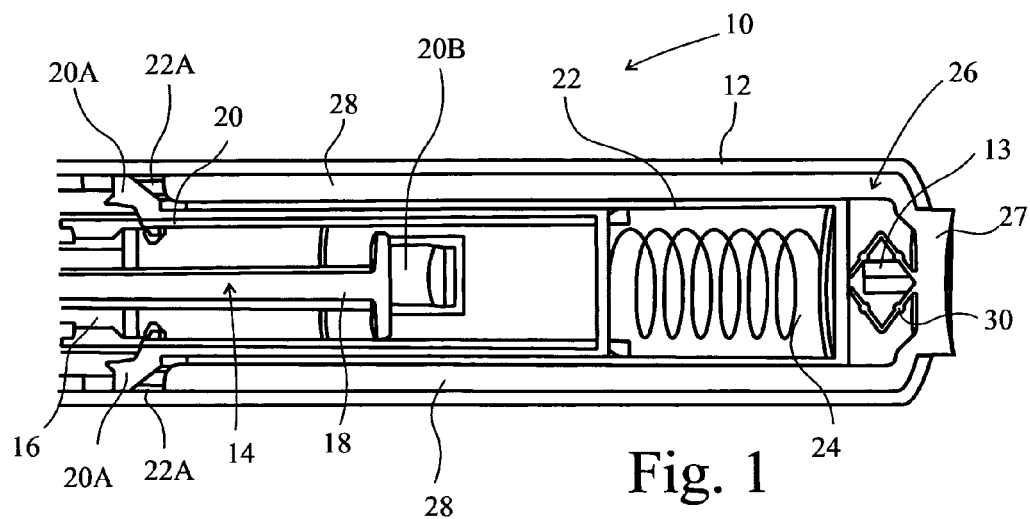
FIG. 1 is a sectional view of part of an autoinjector device according to the present invention and FIG. 1A shows a detailed view of the rear of the device (with a transparent outer housing for clarity)

FIG. 1 shows a sectional view of an exemplary embodiment of an autoinjector device 10 according to present invention. The device 10 has a housing including an outer housing 12 which houses a syringe 14. The syringe 14 is adapted to hold a volume of medicament and comprises a barrel 16, a needle (not shown) at one end of the barrel 16, and a plunger 18, axially moveable within the barrel 16. The needle is axially moveable in and out of a front end of the device's housing but is biased to be normally wholly inside the housing.

The device further comprises an inner housing 20 disposed intermediate the outer housing 12 and at least part of the syringe 14. Prior to actuation for delivery of medicament, at least a part of the inner housing 20 is disposed axially rearward of the barrel 16 of the syringe 14. The device 10 further comprises a spring housing 22 intermediate a portion of the inner housing 20 and the outer housing 12. A spring 24 is located between the spring housing 24 and the inner housing 20 and biases the inner housing 20 axially forward. In alternative embodiments, other energy sources, such as compressed gas, may be used in place of the spring 24. In the embodiment shown in the Figures, the inner housing 20 has a plurality of radially flexible tags 20A that, in a relaxed position, are disposed in apertures 22A of the spring housing 22. With the tags 20A located in apertures 22A, the axial path of the inner housing 20 is blocked by the spring housing 22 and the inner housing 20 is prevented from moving axially forward under the influence of spring 24.

The inner housing 20 is adapted to act on the syringe 14 under the influence of the spring 24 to move at least part of the needle out of the outer housing 12 and then act on the plunger 18 to expel medicament through the needle. These steps are prevented from taking place, however, when the tags 20A of the inner housing 20 are located in the apertures 22A of the spring housing 22.

In order to deliver a dose of medicament, therefore, the user must dislodge the tags 20A from the apertures 22A. To facilitate this, the device is provided with a trigger. In the embodiment shown in the Figures, the trigger comprises a button 26 having a finger pad 27 and axially extending ribs 28. The ribs 28 extend axially forward from the rear of the device 10 in between the inner housing 20 and the outer housing 12 and are axially aligned with the tags 20A (in their relaxed state) of the inner housing 20. The finger pad 27 protrudes through an opening 12A at a rear end 12B of the outer housing 12 allowing access by the user. The button 26 is biased axially rearward from the spring housing 22 by a spring 30, although other biasing means may be envisaged.

Figure 1A:
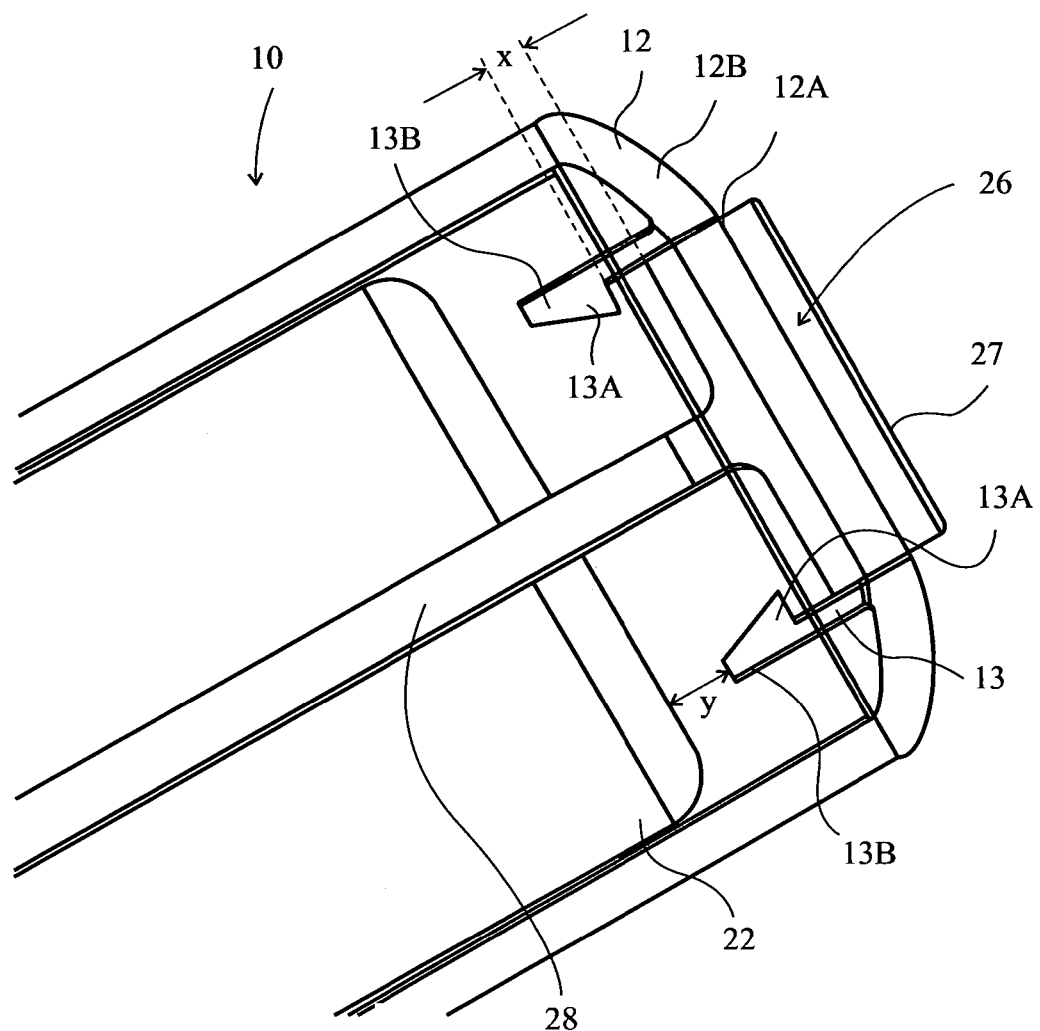

When a front cap (not shown) of the device 10 is removed, the outer housing 12 can be moved axially forward with respect to the spring housing 28 and inner housing 20. The extent of the possible axial displacement of the outer housing 12 relative the spring housing 22 and inner housing 20 is determined by catches 13 (see FIG. 1A) that extend axially forward from the rear end 12B of outer housing 12. The catches 13 each have an axially extending portion 13B and a radially extending portion 13A. When the outer housing 12 is moved axially forward relative to the spring housing 22 and inner housing 20 by a distance y, the axially extending portions 13B of catches 13 abut the spring housing 22 and further axial displacement of the outer housing 12 is prevented.

The button 26 is axially displaceable relative to the outer housing 12. However the extent of relative displacement is also determined by the catches 13. When the button 26 is moved axially forward relative to the outer housing 12 by a distance x, the finger pad 27 abuts radially extending portions 13A of the catches 13 and further axial displacement of the button 26 is prevented.

The button 26 can therefore move axially forward by a total distance x+y relative to the spring housing 28 and inner housing 20 when the outer housing 12 is moved axially forward and the button 26 is depressed by the user. In the particular embodiment shown in the Figures, either action can be done before the other to displace the button 26 by a total distance of x+y relative the spring housing 22 and inner housing 20.

Figure 2:
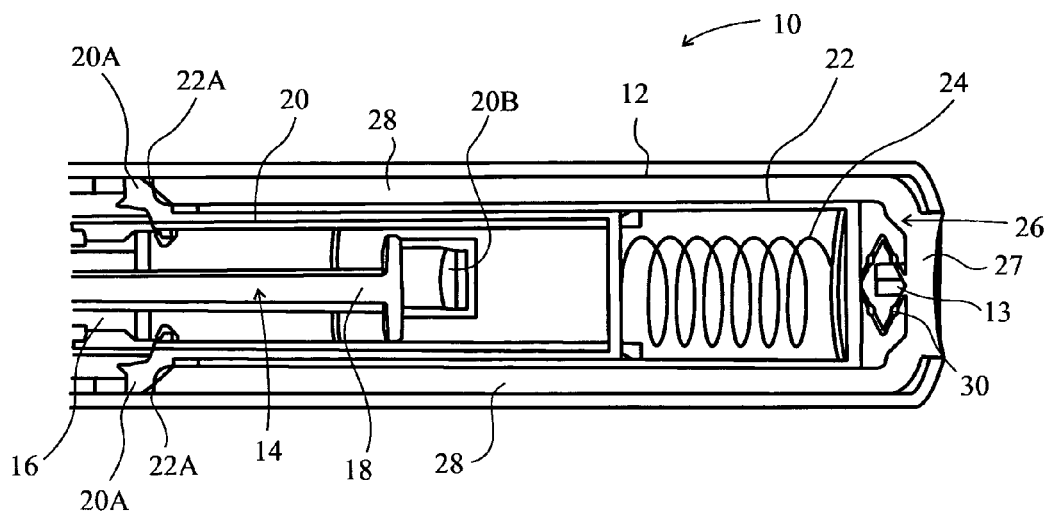
FIG. 2 is a sectional view of the autoinjector device of FIG. 1 with the button depressed.

FIG. 2 shows the device with the button 26 depressed and the outer housing 12 in its original, undisplaced position. In this condition, the ribs 28 have moved a distance x axially forward relative to the inner housing 12 (compared with the device shown in FIG. 1). The displaced ribs 28 may engage with the tags 20A of the inner housing 20, but the displacement x of the ribs 28 is insufficient to unlatch the tags 20A from the apertures 22A.

Figure 3:
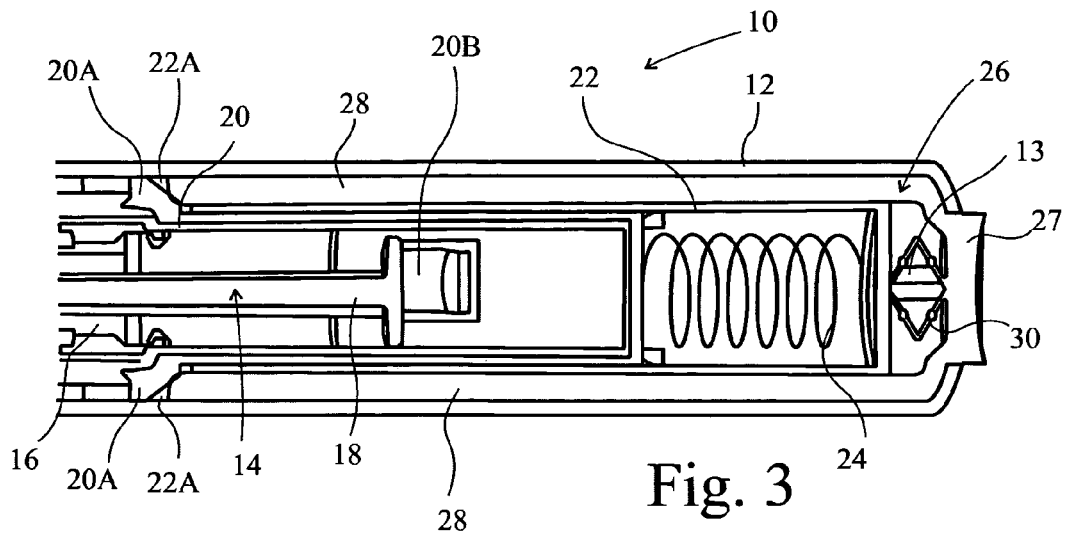
FIG. 3 is a sectional view of the autoinjector device of FIG. 1 with the outer housing moved axially forward.
Figure 4:
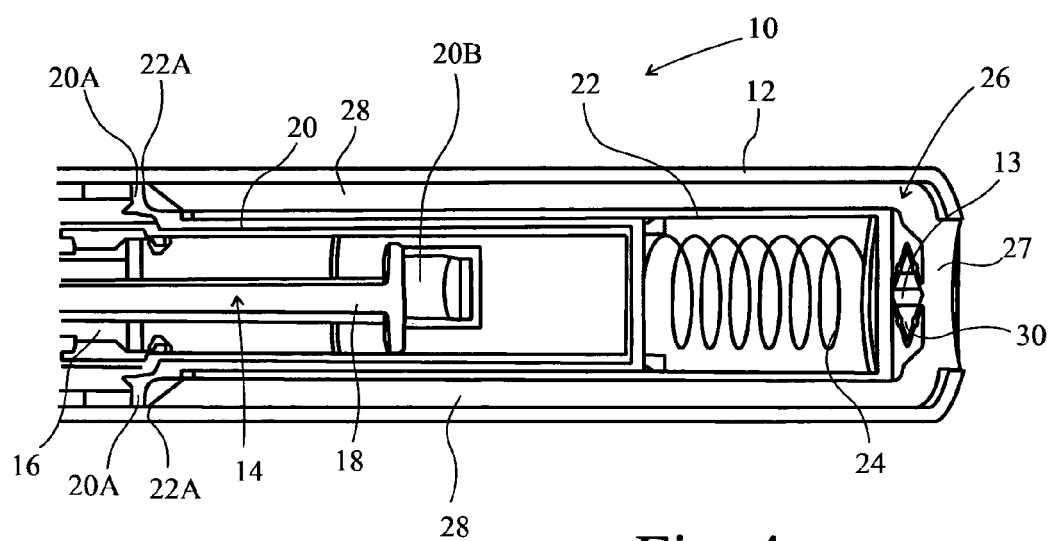
FIG. 4 is a sectional view of the autoinjector device of FIG. 1 with the outer housing moved axially forward and the button depressed.

FIG. 3 shows the device 10 with the outer housing 12 displaced axially by a distance y with respect to the inner housing 20 and spring housing 22. In this position, the button 26, and therefore the ribs 28, are displaced axially a distance y with respect to the inner housing 20 and spring housing 22. The displaced ribs 28 may engage with the tags 20A of the inner housing 20 but do not unlatch the tags 20A from the apertures 22A. As shown in FIGS. 2 and 3, the individual actions of displacing the outer housing 12 and depressing the button 26 are, each in themselves, insufficient to unlatch the radially flexible tags 20A from apertures 22A and actuate the device 10. This is because the ribs 28 must be displaced by a disengagement distance that is greater than the greater of x or y, individually, for actuation to take place. Because of the arrangement of catches 13, the ribs 28 are only permitted to be displaced by the disengagement distance relative the inner housing 20 and spring housing 22 if the button 26 is depressed by a distance x relative the outer housing 12 and the outer housing 12 is moved axially forward by a distance y relative the inner housing 12 to the position shown in FIG. 4. The disengagement distance is less than or equal to the sum x+y. In FIG. 4, the button 26, and therefore the ribs 28, are displaced by a distance x+y relative to the inner housing 12 as compared to the device of FIG. 1.

When displaced by the disengagement distance, the ribs 28 may engage with the tags 20A and cause them to flex radially inward, out of engagement with apertures 22A (FIG. 4 does not show the tags 20A flexed radially inwards but illustrates the extent of interference between the ribs 28 and tags 20A). When the tags 20A are flexed radially inwards, the spring housing 22 is no longer axially aligned with them and so the inner housing 20 is free to move axially forwards under the influence of the spring 24 to expose the needle and deliver a dose of medicament.

In a particularly preferable embodiment, the inwardly flexed tags 20A drive the barrel 16 axially forward to move at least a part of the needle out of the outer housing 12. When the needle extends out of the outer housing by the desired amount, the tags 20A are radially aligned with further apertures that allow them to relax once more, moving radially outward. Preferably at the same time, during needle insertion, a set of rear tags 20B are urged radially inwards into axial alignment with the plunger 18 of the syringe 14. Under the influence of the spring 24, the rear tags 20B move the plunger 18 axially forward with respect to the barrel 18 expelling medicament out of the needle. When a dose of medicament has been delivered, both of sets of tags 20A, 20B are in a relaxed state out of the axial path of the barrel 16 and the needle so that the syringe 14 is free to retract under the influence of a return spring (not shown).

The skilled reader will appreciate that alternative delivery processes are compatible with the actuation mechanism of the present invention and that the above described process represents one of many possible examples. In all embodiments, the device is actuated by the user moving the outer housing 12 relative to the inner housing 20 and actuating a trigger. The button 26 described above is a particularly preferable embodiment of the trigger. However the invention is not limited to button actuation. In alternative embodiments, for example, the trigger may be a slider located on the outer housing 12. In any case, the inner housing is prevented from moving axially forward due to engagement with blocking means or gripping means.

The blocking means may comprise any mechanism that is capable of blocking the axial path of at least part of the inner housing and/or radially gripping the inner housing to prevent the inner housing moving axially forward under the influence of the energy source. For example, the blocking means may be apertures with which a radially extending portion of the inner housing can engage thereby preventing axial movement of the inner housing. Alternatively, the blocking means may be radial components that engage with at least a part of the inner housing. For example, this may be a front portion of the inner housing or apertures in the inner housing.

The blocking means may comprise gripping means in the form of a radially biased component that, for example, is biased radially inwards to grip an outer surface of the inner housing, or is biased radially outwards to grip an inner surface of the inner housing. Frictional forces between the inner housing and the blocking means would then be capable of preventing forward axial movement of the inner housing under the influence of the energy source.

For example, the blocking means may be apertures 22A in the spring housing 22 into which tags 20A of the inner housing 20 can engage thereby blocking the axial path of the tags 20A and therefore the inner housing 20. The inner housing 20 is then prevented from moving axially forward under the influence of the energy source due to the engagement between the tags 20A and apertures 22A.

The movement of the outer housing 12 and actuation of the trigger act together (in any order) to disengage the inner housing 20 from the blocking means and allow delivery to take place. This may be achieved by a disengagement element that may be an element of the outer housing, an element of the trigger, or an element of both. In order to disengage the inner housing 20 from the blocking means, the disengagement element may move or cause the movement of the component previously blocking the axial path of the inner housing to a position where it no longer blocks the axial path of the inner housing. In the case where gripping means are employed to prevent axial movement of the inner housing, the disengagement element may disengage the inner housing from the gripping means by removing the bias from the radially biased component so that the friction between the inner housing and the gripping means is insufficient to prevent forward axial movement of the inner housing. Alternatively, the disengagement element may cause the radially biased components to be counter-biased in the opposite radial direction to reduce the friction between the gripping means and inner housing to a level that is insufficient to prevent forward axial movement of the inner housing.

For example, the disengagement element may be the ends of the ribs 28 which ride against a chamfered surface of tags 20A to urge the tags 20A radially inwards and out of engagement with the apertures 22A. When tags 20A are out of engagement with apertures 22A, the axial path of the tags 20A is clear and the inner housing 20 may move axially forward under the influence of the energy source.

The individual acts of sliding the outer housing 12 axially forward, or actuating the trigger, are not separately capable of actuating the device to deliver a dose of medicament. The user must therefore perform both steps to give an injection and therefore, the risk of accidental firing is minimised.

For a given device, the trigger mechanism can be chosen to be one that is suitable for use with a particular drug or is preferred by a particular type of patient. The trigger mechanism on an emergency autoinjector for delivering adrenaline, for example, may be different to the trigger mechanism on a device designed to be used frequently such as an insulin autoinjector for a diabetic patient. Similarly, the trigger mechanism on an autoinjector designed to be used by the patient may be different to the trigger mechanism on an autoinjector designed to be used by a medical practitioner. The skilled reader will appreciate that the trigger may be a button or a slider, or any other interface component that may be actuated by the user to bring about a mechanical effect.

The present invention allows a familiar, and therefore, perhaps, more user-friendly, actuation means to be applied to an improved autoinjector device. This has the surprising effect of providing a relatively more complicated device (as compared with that described in EP-B-1715903) in order to provide an exterior mechanism that is appears consistent with known autoinjectors with which the user may already be familiar. Familiarity, intuitiveness and ease of use are three very important factors to consider in providing a user with a safe and reliable autoinjector.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. An injection device comprising an outer housing adapted to receive: a syringe for holding a volume of a medicament, said syringe comprising a barrel, a needle at one end of the barrel, and a plunger, axially moveable within the barrel, the needle and barrel being such that at least part of the needle is axially moveable in and out of said outer housing but is biased to be normally wholly inside said housing; the injection device further comprising: an inner housing intermediate the outer housing and at least part of the barrel and/or plunger; an energy source in communication with the inner housing; and blocking means capable of preventing said inner housing moving axially under the influence of said energy source; the device being moveable between two positions, namely a first position in which the inner housing is prevented from moving axially forward by engagement with said blocking means; and a second position in which the inner housing is disengaged from said blocking means and is capable of acting on the syringe under the influence of said energy source to move said at least part of the needle out of said outer housing; wherein said device is moveable from said first position to said second position by movement of said outer housing relative to said inner housing and actuation of a trigger.

2. The injection device according to claim 1, wherein said movement of said outer housing relative to said inner housing and said actuation of a trigger are two distinct user-performed actions.

3. The injection device according to claim 1, wherein said inner housing is biased axially forward by said energy source in said first position.

4. The injection device according to claim 1, further comprising a spring housing intermediate said outer housing and said inner housing.

5. The injection device according to claim 1, wherein said blocking means prevents said inner housing moving axially forward under the influence of said energy source by blocking the axial path of at least part of said inner housing.

6. The injection device according to claim 1, wherein said blocking means comprises a radially moveable component that can be radially urged against a surface of said inner housing so that friction prevents said inner housing moving axially forward under the influence of said energy source.

7. The injection device according to claim 1, wherein said trigger comprises a disengagement element and, upon actuation of the trigger, said disengagement element is capable of disengaging said inner housing from said blocking means to allow said device to move into said second position.

8. The injection device according to claim 7, wherein said disengagement element comprises axially extending ribs.

9. The injection device according to claim 8, wherein said ribs are axially moveable with respect to said inner housing and are adapted to disengage said inner housing from said blocking means upon axially moving relative to said inner housing.

10. The injection device according to claim 9, wherein ribs disengage said inner housing from said blocking means upon axially moving relative to said inner housing by a disengagement distance;

and in said first position, said ribs are axially moveable relative to said outer housing by a first distance and said outer housing is axially moveable relative to said inner housing by a second distance;

where said first distance plus said second distance is greater than or equal to said disengagement distance.

11. The injection device according to claim 10, wherein in said first position, axial movement of said ribs is limited relative to said outer housing to not exceed said first distance, and axial movement of said outer housing is limited relative to said inner housing to not exceed said second distance.

12. The injection device according to claim 11, wherein in said first position, axial movement of said ribs is limited relative to said outer housing and axial movement of said outer housing is limited relative to said inner housing by at least one catch on said outer housing;
   where each of said at least one catch has an axially extending portion that abuts said spring housing or a component fixed axially thereto to limit relative displacement between said outer housing and said inner housing, and a radially extending portion that is in axial alignment with at least a portion of said trigger to limit relative displacement between said ribs and said outer housing.

13. The injection device according to claim 1, wherein said trigger comprises a button and said trigger is actuated by depressing said button.

14. The injection device according to claim 13, wherein said trigger comprises a disengagement element comprising axially extending ribs, wherein said button is connected to said ribs and depression of said button proportionally moves said ribs axially forward relative to said outer housing.

15. The injection device according to claim 13, wherein said inner housing comprises a plurality of radially flexible tags, and said blocking means comprises apertures in said spring housing for receiving said flexible tags and preventing forward axial movement of said inner housing in said first position.

16. The injection device according to claim 14, wherein said ribs are adapted to contact said flexible tags and cause said tags to flex radially inwards, out of said apertures, to disengage said inner housing from said blocking means.

17. The injection device according to claim 1, wherein in said second position, the inner housing acts on the barrel of said syringe to move said at least part of the needle out of said outer housing.

18. The injection device according to claim 15, wherein from said second position, the device is moveable into a third position in which the inner housing acts on the plunger but not the barrel such that, in use, said plunger is moveable axially into said barrel so as to expel medicament through the needle.

19. The injection device according to claim 1, wherein said trigger is mounted on said outer housing.

20. The injection device according to claim 1, wherein said energy source is a spring.

21. The injection device according to claim 1, wherein said energy source is compressed gas.

* * * * *